US00PP26672P3

(12) United States Plant Patent
Danziger

(10) Patent No.: US PP26,672 P3
(45) Date of Patent: Apr. 26, 2016

(54) ***HEUCHERA* PLANT NAMED 'DKIRA88'**

(50) Latin Name: ***Heuchera* hybrid**
Varietal Denomination: DKIRA88

(71) Applicant: Gavriel Danziger, Moshave Mishmar Hashiva (IL)

(72) Inventor: Gavriel Danziger, Moshave Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 96 days.

(21) Appl. No.: 13/999,985

(22) Filed: Apr. 11, 2014

(65) Prior Publication Data

US 2015/0296679 P1 Oct. 15, 2015

(51) Int. Cl.
*A01H 5/12* (2006.01)

(52) U.S. Cl.
USPC ..... Plt./440

(58) Field of Classification Search
USPC ..... Plt./440
See application file for complete search history.

*Primary Examiner* — Susan McCormick Ewoldt
(74) *Attorney, Agent, or Firm* — Cassandra Bright

(57) ABSTRACT

A new and distinct *Heuchera* cultivar named 'DKIRA88' is disclosed, characterized by a compact and mounded habit, greyed-orange leaves with red-purple venations and fast growth rate. The new variety is a *Heuchera*, normally produced as an outdoor garden or container plant.

2 Drawing Sheets

Figure 1:
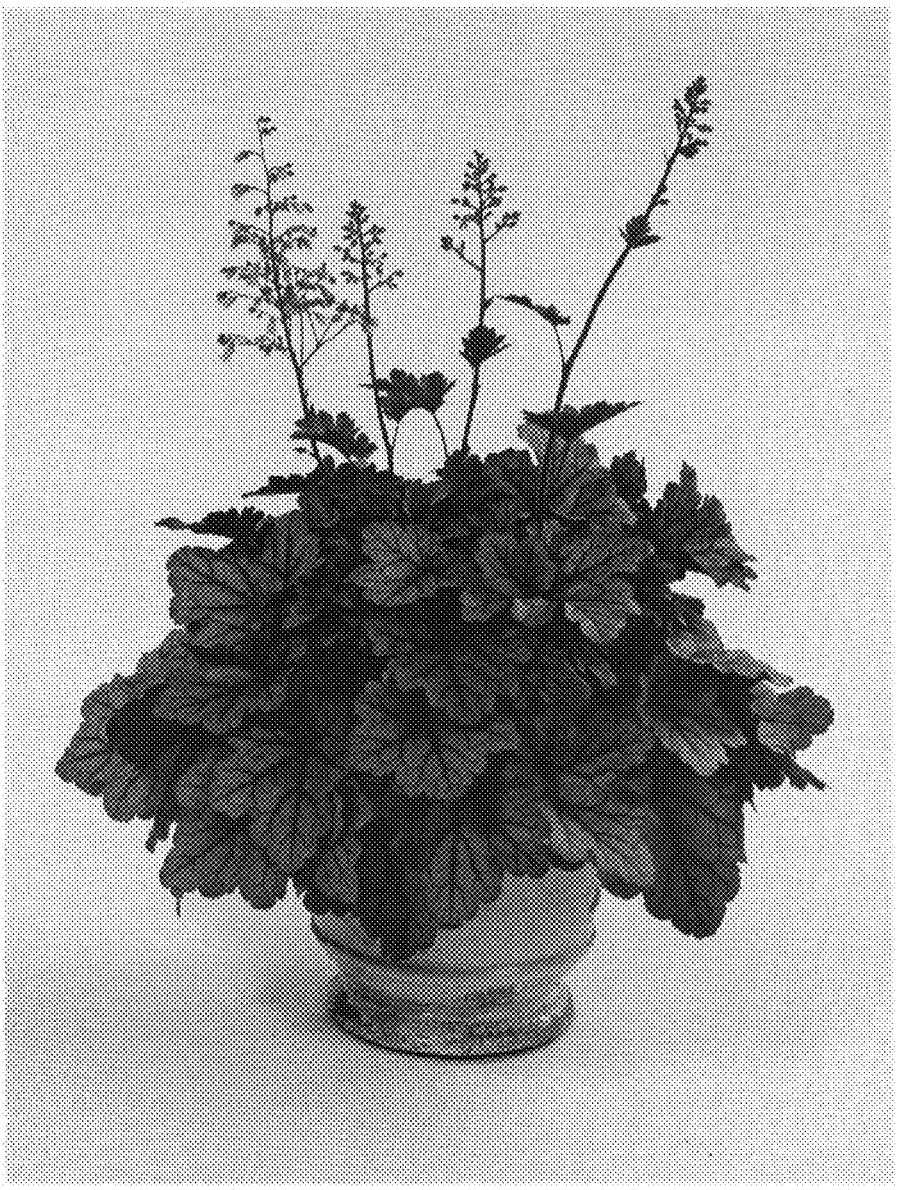

Latin name of the genus and species: *Heuchera* hybrid.
Variety denomination: 'DKIRA88'.

BACKGROUND OF THE INVENTION

The new *Heuchera* cultivar is a product of a planned breeding program conducted by the inventor, Gavriel Danziger, in Moshav Mishmar Hashiva, Israel. The objective of the breeding program was to produce new *Heuchera* varieties for ornamental commercial applications. The cross resulting in this new variety was made during February of 2009.

The seed parent is the unpatented, proprietary variety referred to as *Heuchera* hybrid 'HU-8-149'. The pollen parent is the unpatented, proprietary variety referred to as *Heuchera* hybrid 'HU-8-116'. The new variety was discovered in November of 2009 by the inventor in a group of seedlings resulting from the 2009 crossing, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel in November of 2009 and has shown that the unique features of this cultivar are stable and reproduced true to type in more than 50 successive generations.

SUMMARY OF THE INVENTION

The cultivar 'DKIRA88' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DKIRA88' These characteristics in combination distinguish 'DKIRA88' as a new and distinct *Heuchera* cultivar:

1. Compact and mounded plant habit.
2. Greyed-orange to greyed-green leaf with red-purple venation.
3. Rapid growth rate.

Plants of the new cultivar 'DKIRA88' are similar to plants of the seed parent, *Heuchera* 'HU-8149' in most horticultural characteristics, however, plants of the new cultivar 'DKIRA88' differs in the following;

1. Foliage is greyed-orange. The seed parent foliage is red-silver.
2. Fuller plant body structure.

Plants of the new cultivar 'DKIRA88' are similar to plants of the pollen parent; *Heuchera* 'HU-8-116' in most horticultural characteristics, however, plants of the new cultivar 'DKIRA88' differs in the following;

1. Foliage is greyed-orange. The pollen parent foliage is green-orange.
2. Fuller plant body structure.
3. Flowers are red-white; flowers of pollen parent are pink-white.

COMMERCIAL COMPARISON

Plants of the new cultivar 'DKIRA88' are comparable to the variety *Heuchera* 'Strawberry Candy' U.S. Plant Pat. No. 12,195. The two *Heuchera* varieties are similar in most horticultural characteristics; however, the new variety 'DKIRA88' differs in the following:

1. Leaf main color of candidate variety is greyed-red compared to green of comparison variety.
2. Flower color of candidate variety is light pink compared to dark pink of comparison variety.
3. Leaf underside color of candidate variety is purple compared to green of comparison variety.
4. Inflorescence of the new variety is occurs above, but, closer to the foliage than comparator variety.

BRIEF DESCRIPTION OF THE PHOTOGRAPHS

The accompanying photograph in FIG. 1 illustrates in full color a typical plant of 'DKIRA88' grown in a greenhouse, in a 16 cm pot. Age of the plant photographed is approximately 4 months from a rooted cutting.

Figure 2:
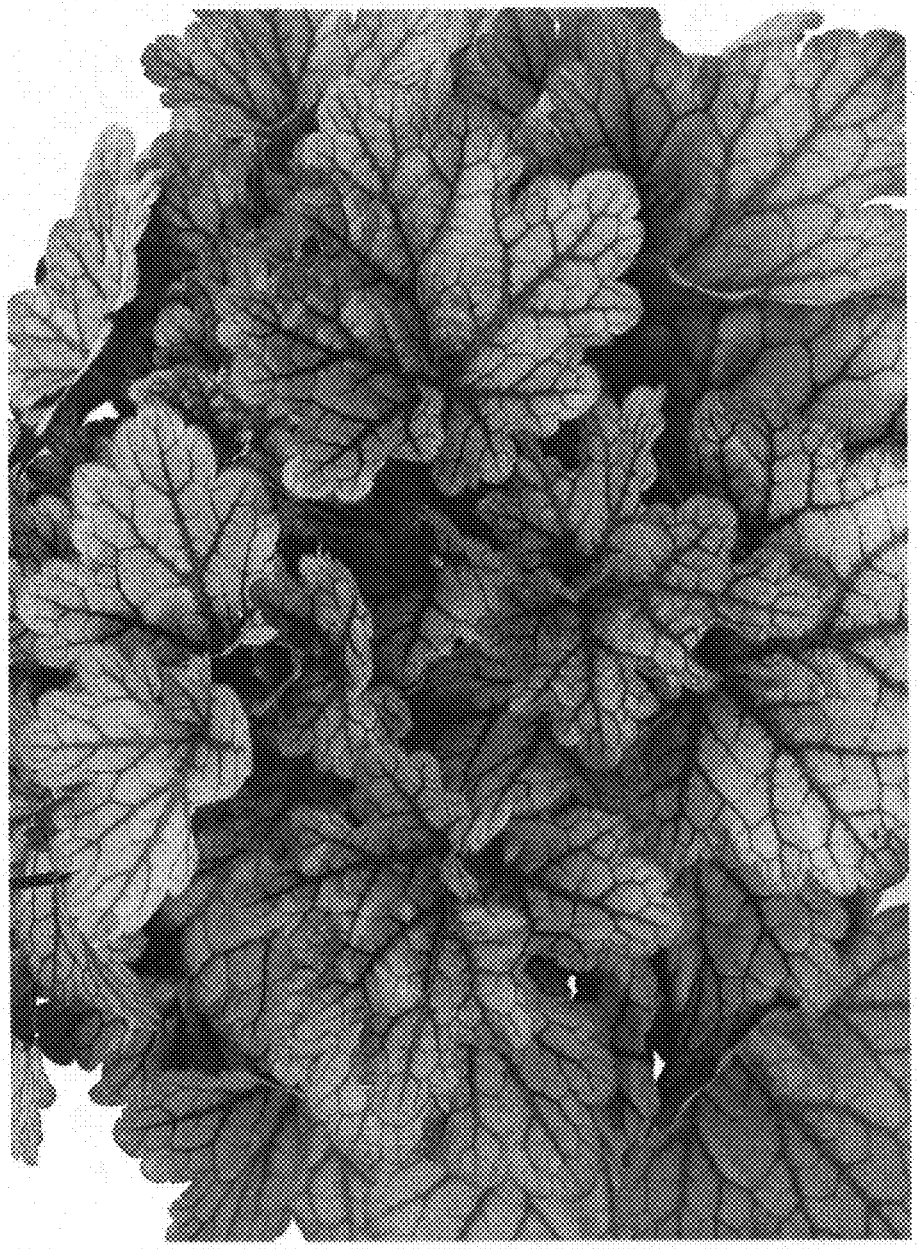

FIG. 2 illustrates a close up of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DKIRA88' plants grown in a greenhouse, in Moshav Mishmar Hashiva, Israel. The growing temperature ranged from 18° C. to 28° C. during the day and from 13° C. to 18° C. during the night. General light conditions are bright, normal sunlight. Measurements and numerical values represent averages of typical plant types.

Botanical classification: *Heuchera* hybrid 'DKIRA88'.

PROPAGATION

Type of propagation typically used: Cutting.

Time to initiate roots: About 12 days at approximately 25° C.

Root description: Fleshy, fibrous.

PLANT

Age of plant described: Approximately 16 weeks.

Growth habit: Mounded.

Height: Approximately 12-15 cm. to top of foliage. (When flowering—height is 50-60 cm to top of flowers).

Plant spread: Approximately 20-25 cm.

Growth rate: Rapid.

Branching characteristics: No lateral branches, foliage emerges from basal rosette.

FOLIAGE

Leaf:

*Arrangement.*—Rosette — Single.

*Compound or single.*—Single.

*Shape of blade.*—Overall shape deltoid, with broad, shallow lobes.

*Average length.*—Approximately 6-8 cm.

*Average width.*—Approximately 6-10 cm.

*Apex.*—Broadly obtuse, lobed.

*Base.*—Cordate.

*Attachment.*—Petiolate.

*Margin.*—Crenate, faintly ciliate.

*Texture of top surface.*—Slightly rough (because of venation), slight pubescence.

*Texture of bottom surface.*—Slightly rough (because of venation).

*Leaf internode length.*—No internodes.

*Color.*—Marbled effect of dark veins with silver-green inter-venal areas. Color change with seasons not observed. Foliage color difference occur with age of leaves. Young foliage upper side: Greyed-orange group 177B Near RHS. Young foliage under side: Near greyed-purple 185A RHS. Mature foliage upper side: Near greyed-green 179A RHS. Mature foliage under side: Near Red-purple 59B RHS.

*Venation.*—Type: Reticulated. Venation color upper side: Near Red-purple 59A RHS. Venation color under side: Near Red-purple 59B RHS.

*Durability of foliage to stresses.*—Highly durable to full sun exposure, hail, heavy rain, drought.

Petiole:

*Average length.*—Approximately 6-8 cm.

*Diameter.*—Approximately 0.15-0.2 cm.

*Color.*—Near Approximately Red purple 64B.

*Strength.*—Strong, flexible, not easily breaking.

Other foliage characteristics: Slightly metallic sheen.

FLOWER

Bloom period:

*Natural season.*—Under moderate climate such as in Israel — will bloom continuously from Winter to early Summer. Under typical European weather, will bloom from May through August in the Northern Hemisphere.

Bud:

*Bud shape.*—Bulbous.

*Bud diameter.*—Approximately 0.2 cm.

*Bud color.*—Near Yellow-green N144A RHS.

*Base/calyx.*—Near red-purple 60B RHS.

Inflorescence: Raceme.

*Diameter.*—10-15 cm.

*Depth.*—20.

*Flowers per raceme.*—30-50 open and 50 buds.

Peduncle:

*Length.*—Approximately 30 cm.

*Diameter.*—Approximately 0.3-0.5 cm.

*Angle.*—Erect.

*Strength.*—Strong.

*Texture.*—Soft and silky, slightly pubescent, slightly metallic.

*Color.*—Near red-purple 59A RHS.

Individual flower:

*Arrangement and type.*—Number of single flowers that arranged on evenly feathery conical panicles on upper half of flowering stem; usually about 100 to 150 flowers per flowering stem. Flowering stems uniform in shape and dense with numerous flowers. Flowering continuously with numerous flowering stems forming throughout flowering period; usually about 10 to 15 flowering stems per plant. Flowering stems often produce small lateral leaves.

*Shape.*—Campanulate.

*Quantity of flowers and buds per plant.*—Approximately 200-300 open flowers.

*Diameter of entire flower.*—Approximately 0.7 cm.

*Depth of flower.*—Approximately 0.7 cm.

*Rate of opening.*—Individual flowers: Fully open approximately 3 days from the bud stage.

*Flower longevity on plant.*—Approximately 7 days.

*Persistent or self-cleaning.*—Self cleaning.

*Fragrance.*—Not detected.

Petals:

*Length of petal.*—Approximately 0.4 cm.

*Width of petal.*—Approximately 0.15 cm.

*Apex.*—Acute.

*Shape of petal.*—Spatulate.

*Petal margin.*—Entire.

*Petal arrangement.*—Rotate.

*Petal number.*—5.

*Petals fused.*—No.

*Petal appearance.*—Matte.

*Petal texture.*—Smooth and silky, slightly pubescent.

Color:

*Upper surface at first opening.*—Near white 155A RHS.
*Upper surface at maturity.*—Near white 155A RHS.
*Upper surface at fading.*—Near white 155B RHS.
*Under surface at first opening.*—Near white 155A RHS.
*Under surface at maturity.*—Near white 155A RHS.
*Under surface at fading.*—Near white 155B RHS.

Pedicel:

*Length.*—Approximately 0.7 cm.
*Diameter.*—Approximately 0.05 cm.
*Angle.*—Erect at first, when mature — Horizontal to 45 degrees downwards towards the stem.
*Strength.*—Strong, does not break easily.
*Texture.*—Smooth and silky, slightly pubescent.
*Color.*—Near red-purple 60C RHS.

Sepal:

*Number.*—5 (fused at base).
*Sepal appearance.*—Matte.
*Sepal arrangement.*—Five sepals fused into a radial symmetrical calyx tube.
*Sepal texture.*—Thin, smooth and silky, slightly pubescent.
*Sepal length.*—Approximately 0.7 cm.
*Sepal width.*—Approximately 0.2 cm.
*Sepal shape.*—Oblong.
*Base.*—Attenuate.
*Apex shape.*—Obtuse.
*Margin.*—Entire.
*Color upper surface.*—Near yellow group 11C RHS.
*Color lower surface.*—Near greyed-green 195A RHS.

REPRODUCTIVE ORGANS

Stamens:

*Number.*—5.
*Filament length.*—About 0.5 cm.

Anthers:

*Length.*—About 0.2 cm.
*Shape.*—Oval.
*Color.*—Near Orange 24A RHS.
*Pollen.*—Color: Near greyed-orange 168A RHS. Quantity: Moderate.

Pistil:

*Number.*—2.
*Length.*—About 0.6 cm.
*Style.*—Length: About 2 cm. Color: RHS Yellow-Green 154 C.
*Stigma.*—Shape: Rounded. Color: Near White 155A RHS. Ovary Color: Near Green-yellow 1A RHS.

OTHER CHARACTERISTICS

Disease/pest resistance: Neither resistance nor susceptibility to normal diseases and pests of *Heuchera* have been observed.

Drought tolerance and cold tolerance: Hardy perennial USDA zone 4. Tolerates some drought without significant damage to plant.

Fruit/seed production:

*Color and shape of fruits and seeds.*—Dark Brown seeds, Bean Shape, 0.1 cm length×0.05 cm wide. Too minute to measure color with RHS.

What is claimed is:

1. A new and distinct cultivar of *Heuchera* plant named 'DKIRA88' as herein illustrated and described.

* * * * *